United States Patent [19]

Winters

[11] Patent Number: 4,873,983

[45] Date of Patent: Oct. 17, 1989

[54] STEERABLE GUIDEWIRE FOR VASCULAR SYSTEM

[75] Inventor: R. Edward Winters, Andover, Mass.

[73] Assignee: Advanced Biomedical Devices, Inc., Andover, Mass.

[21] Appl. No.: 148,906

[22] Filed: Jan. 27, 1988

[51] Int. Cl.⁴ ............................................. A61M 25/00
[52] U.S. Cl. .................................... 128/657; 128/772; 604/282
[58] Field of Search ............... 128/772, 657, 656, 658; 604/280, 282, 264, 281, 283

[56] References Cited

U.S. PATENT DOCUMENTS

| | | | |
|---|---|---|---|
| 3,789,841 | 2/1974 | Antoshkiw | 128/657 |
| 4,215,703 | 8/1980 | Willson | 128/772 |
| 4,456,017 | 6/1984 | Miles | 128/772 |
| 4,538,622 | 9/1985 | Samson et al. | 128/772 |
| 4,545,390 | 10/1985 | Leary | 128/772 |
| 4,554,929 | 11/1985 | Samson et al. | 128/772 |
| 4,586,923 | 5/1986 | Gould et al. | 128/657 |
| 4,619,274 | 10/1986 | Morrison | 128/657 X |
| 4,676,249 | 6/1987 | Arenas et al. | 604/164 X |
| 4,719,924 | 1/1988 | Crittenden et al. | 128/657 X |
| 4,724,846 | 2/1988 | Evans | 128/657 X |

Primary Examiner—Max Hindenburg
Assistant Examiner—John P. Lacyk
Attorney, Agent, or Firm—Bernard, Rothwell & Brown

[57] ABSTRACT

A guidewire arranged to be transported through the vascular system composed of a helically wound tapered spring, a length of tubing attached to the proximal end of the spring, a wire attached to the inner surface of and extending to the tip of the spring for curving the tip to a desired shape, and a tapered core wire moveably disposed in the tubing and spring and or sufficient length to extend to the tip of the spring to vary the stiffness and curvature of the tip.

5 Claims, 1 Drawing Sheet

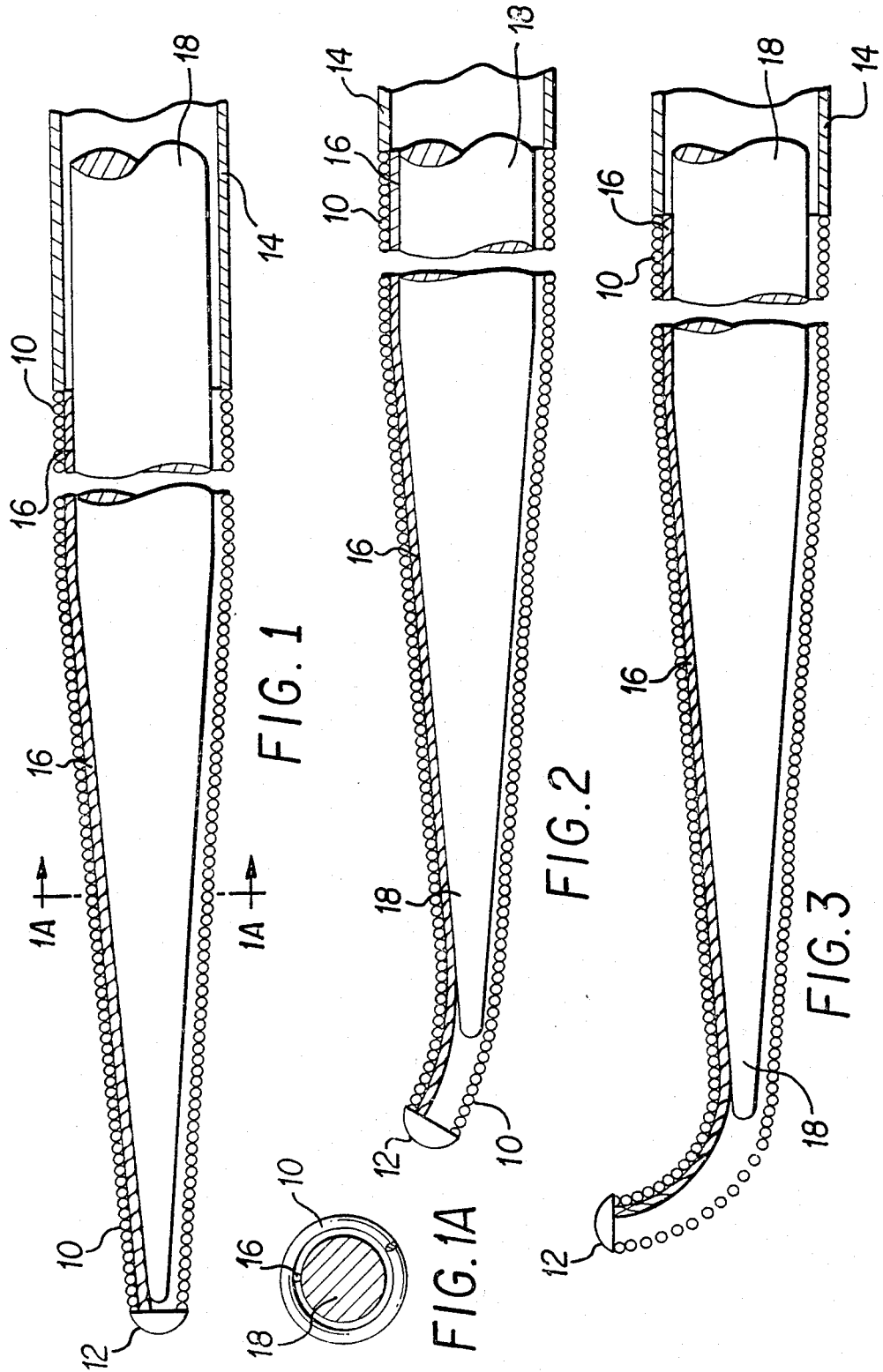

STEERABLE GUIDEWIRE FOR VASCULAR SYSTEM

BACKGROUND OF THE INVENTION

1. Field of the Invention

The invention is related to guidewires used for the insertion of catheters into the vascular system as a method of treating coronary arterial vascular blockage.

2. Description of the Prior Art

As a treatment technique for removing blockages in the vascular system, particularly those which affect the blood supply to the heart, guidewires of very fine diameter are inserted directly into the system from outside the patient and manipulated or steered by the physician or practitioner through the system to the blockage by fluoroscopic observation. Since the various arteries through which the wire must pass are sinuous or irregular in shape and intersect and connect with other vessels at various and sometimes sharp angles, maneuvering the wire to the position of concern is a delicate task. A plurality of guidewire type devices designed for this purpose exist in the prior art.

Each is a novel approach to the problem of providing the user with sufficient control to transverse the vascular system in a speedy and careful manner.

For example, U.S. Pat. Nos. 4,545,390, Leary, and 3,789,841, Antoshkiw, both show distal tips formed of helically wound springs surrounding fixed tapered cores. U.S. Pat. No. 3,631,848, Muller, describes an axially movable distal tip extension tube of relatively short length.

A coil tip with tapered face edges which will curve toward the taper when pulled upon by an internal control wire is disclosed in U.S. Pat. Nos. 3,452,740, and 3,452,742, both to Muller. U.S. Pat. No. 4,650,467, Bonello shows a similar arrangement for inclining the tip by retraction of a control wire affixed thereto.

Additionally, U.S. Pat. No. 3,528,406, Jeckel et al. teaches the use of a fixed core wire having a reduced diameter in the spring tip portion of the wire. U.S. Pat. No. 3,625,200, Muller, discloses a curvable tip comprising solid cylindrical links engaging each other with ball and socket joints each of which is manipulatable by a fine core wire. Finally, U.S. Pat. No. 4,573,470, Samson shows a curved tip which is rotated in its entirety by rotating a core wire at the control handle.

The present invention is an improved guidewire which allows the user to vary the stiffness of the wire and vary the curvature of the tip from outside the patient during the transport and manipulation process.

SUMMARY OF THE INVENTION

The invention may be summarized as a guidewire of the type of and for the above described purpose consisting of a distal portion comprising a helically wound tapered spring having a smooth rounded tip, and a proximal portion comprising a length of tubing joined at the proximal end of the spring to form a continuous unit. A core wire tapered at the distal end is moveably disposed within the tubing and spring such that the amount of flexibility or floppiness of the spring may be varied by moving the core wire to various positions along the length.

An additional fine diameter safety wire is disposed within the tip end of the spring which prevents the spring coils from separating and allows a shape to be imparted to the tip. The safety wire is sufficiently thin to allow the tapered core wire to be positioned to the very tip of the spring. Thus with the core wire partially withdrawn, the end of the spring may assume a curve as a result of the bias of the safety wire. With the core wire fully extended, the curve is removed and the spring tip is straightened facilitating the penetration (crossing) of the lesion or partial blockage, the removal or reduction of which is the object of the technique.

These and other features and objects of the invention will become more clear from the following drawings and description of the preferred embodiment.

DESCRIPTION OF THE DRAWINGS

FIG. 1 is a cross sectional view of the preferred embodiment;

FIG. 1A is a cross-sectional view along line 1A—1A of FIG. 1;

FIG. 2 is an additional cross sectional view of the embodiment of FIG. 1; and

FIG. 3 is a further cross sectional view of the preferred embodiment.

DESCRIPTION OF THE PREFERRED EMBODIMENT

Referring to FIG. 1 there is shown a cross sectional view of the steerable guidewire which comprises the preferred embodiment of the invention. Helically wound spring 10 composing the distal portion of the wire is tapered outward from tip 12 toward tubing 14. The amount or angle of taper and correspondingly the length of the coil are a matter of choice as dictated by clinical requirements. A coil length of 30 centimeters has been found appropriate and as will be obvious, the proximal portion of the coil may have little or no taper, the critical region being that nearest the tip. In the illustrated embodiment, the coil is substantially uniformly tapered.

A safety wire 16 which has sufficient rigidity to hold an imparted shape is attached to the inner surface of spring 10 to provide bias for curving the tip and to prevent the coils of the spring from stretching apart upon retraction. As shown in the drawings, a core wire 18 is provided, which is substantially uniformly tapered rearwardly from the core wire tip. Tapered core wire 18 is disposed within spring 10 and tubing 14 and extends as does tubing 14 a selected length to allow the user to place the core wire at various positions within the spring from outside the patient. A length of approximately 150 centimeters has been found appropriate for this purpose.

FIGS. 2 and 3 show the attitude that the tip will assume when the core is partially withdrawn. FIG. 2 illustrates the partial curve of the tip, the core still acting in part to counter the bias of wire 16 and FIG. 3 shows the core sufficiently withdrawn to allow the tip to reach its full bent, which, according to the illustrated embodiment, is the tip position shown in FIG. 3. As can be seen in FIG. 3, the helically wound spring 10 is tapered along the entire length of the curved position thereof when the tip is in the full bent position shown in FIG. 3.

As is now evident, the invention disclosed herein allows a range of flexibility and control previously unavailable in the art. The wire may be varied from a straight stiff configuration for penetrating or crossing lesions to a curved flexible profile of infinitely varying degree for steering through the junctions, twists and turns of the vascular system.

The materials of which the invention is constructed as well as the technique of use of the wire once in place to receive a catheter are well known and thus not herein described in detail. Similarly the control handle for holding the tubing and moving the core at the proximal end is a device of simple construction of the type described in the prior art referenced above.

Accordingly, the invention is defined by the following claims.

What is claimed is:

1. A steerable guidewire arranged to be transported through the vascular system comprising in combination:
    a. a helically wound tapered spring terminating at the distal end in a smooth rounded tip;
    b. a length of tubing attached to the proximal end of said spring;
    c. a safety wire disposed within and attached to the inner surface of said spring, said wire extending to the tip of said spring, said wire having sufficient rigidity to allow said spring to be curved at its distal end; and
    d. a tapered core wire moveably disposed within said tubing and said spring; the tip of said core wire arranged to be extended to the inner tip of said spring whereby the distal end of said spring will be variably stiffened and straightened according to the position of said core wire within said spring.

2. A steerable guidewire arranged to be transported through a patient's vascular system comprising in combination:
    (a) a helically wound, substantially uniformly tapered spring terminating at a distal end thereof in a smooth rounded tip;
    (b) a length of tubing attached to a proximal end of said spring;
    (c) a biased safety wire disposed within and connected to the inner surface of said spring, said wire extending to the tip of said spring, said wire having sufficient rigidity and bias to allow said spring to be curved at its distal end between a full bent position thereof and a substantially straight position thereof, wherein the helically wound spring is tapered along the entire length of the curved portion of the spring when the distal end thereof is in said full bent position; and
    (d) a tapered core wire movably disposed within said tubing and said spring; said core wire having a tip arranged to be extended to the inner tip of said spring whereby the distal end of said spring will be variably stiffened and straightened according to the position of said core wire within said spring.

3. The guidewire of claim 2 wherein said safety wire is attached to the inner surface of said spring.

4. The guidewire of claim 2 wherein the tapered spring is about 30 cm in length.

5. The guidewire of claim 2 wherein the core wire is tapered rearwardly from its tip.

* * * * *